United States Patent
Lei et al.

(10) Patent No.: US 9,144,550 B2
(45) Date of Patent: Sep. 29, 2015

(54) PREPARATION METHOD OF THE SOLID FORMULATION OF CLOPIDOGREL BISULFATE

(71) Applicants: Jifeng Lei, Shanghai (CN); Ping Sha, Shanghai (CN); Ronggen Jin, Shanghai (CN); Yuwen Shi, Shanghai (CN); Xinhua Shen, Shanghai (CN)

(72) Inventors: Jifeng Lei, Shanghai (CN); Ping Sha, Shanghai (CN); Ronggen Jin, Shanghai (CN); Yuwen Shi, Shanghai (CN); Xinhua Shen, Shanghai (CN)

(73) Assignee: Shanghai Anbison Laboratory Co., Ltd. (CN)

( * ) Notice: Subject to any disclaimer, the term of this patent is extended or adjusted under 35 U.S.C. 154(b) by 0 days.

(21) Appl. No.: 14/615,177

(22) Filed: Feb. 5, 2015

(65) Prior Publication Data

US 2015/0150815 A1 Jun. 4, 2015

Related U.S. Application Data

(60) Division of application No. 13/567,676, filed on Aug. 6, 2012, now abandoned, which is a continuation of application No. PCT/CN2010/073879, filed on Jun. 12, 2010.

(30) Foreign Application Priority Data

Feb. 5, 2010 (CN) .......................... 2010 1 0106188

(51) Int. Cl.
*A61K 9/20* (2006.01)
*A61K 31/4365* (2006.01)

(52) U.S. Cl.
CPC ............. *A61K 9/2095* (2013.01); *A61K 9/2009* (2013.01); *A61K 31/4365* (2013.01)

(58) Field of Classification Search
None
See application file for complete search history.

(56) References Cited

U.S. PATENT DOCUMENTS

| | | | |
|---|---|---|---|
| 4,591,592 A | 5/1986 | Chowhan |
| 4,847,265 A | 7/1989 | Badorc et al. |
| 5,576,328 A | 11/1996 | Herbert et al. |
| 6,429,210 B1 | 8/2002 | Bousquet et al. |
| 6,504,030 B1 | 1/2003 | Bousquet et al. |
| 6,767,913 B2 | 7/2004 | Lifshitz et al. |
| 6,914,141 B2 | 7/2005 | Sherman |
| 2007/0003628 A1 | 1/2007 | Liversidge et al. |
| 2009/0187022 A1 | 7/2009 | Finkelstein et al. |
| 2009/0264460 A1 | 10/2009 | Mishra et al. |

FOREIGN PATENT DOCUMENTS

| | | |
|---|---|---|
| CN | 100400035 C | 7/2008 |
| CN | 101212954 A | 7/2008 |
| CN | 101590023 A | 12/2009 |
| CN | 101766573 A | 7/2010 |
| EP | 1970054 A2 | 9/2008 |
| KR | 20090092106 A | 8/2009 |
| WO | 0001364 A1 | 1/2000 |
| WO | 2004098593 A1 | 11/2004 |
| WO | 2005048992 A1 | 6/2005 |
| WO | 2006044548 A2 | 4/2006 |
| WO | 2007008045 A1 | 1/2007 |
| WO | 2007091279 A1 | 8/2007 |
| WO | 2008059298 A2 | 5/2008 |
| WO | 2008072836 A1 | 6/2008 |
| WO | 2008072939 A1 | 6/2008 |

OTHER PUBLICATIONS

International Search Report; Application No. PCT/CN2010/073879; Issued: Oct. 19, 2010; Mailing Date: Nov. 11, 2010; 3 pages.

*Primary Examiner* — Hasan Ahmed
(74) *Attorney, Agent, or Firm* — St. Onge Steward Johnston & Reens LLC

(57) ABSTRACT

A solid formulation of clopidogrel bisulfate and its preparation method are disclosed. The formulation includes clopidogrel bisulfate as active ingredient, colloidal silicon dioxide as anti-adherent/coating and the carriers selected from diluent, binder, glidant, disintegrant and/or lubricant.

12 Claims, No Drawings

PREPARATION METHOD OF THE SOLID FORMULATION OF CLOPIDOGREL BISULFATE

FIELD OF THE INVENTION

This invention relates to a method of preparation of Clopidogrel bisulfate tablets.

BACKGROUND OF THE INVENTION

Chemically Clopidogrel bisulfate is methyl (+)-(S)-α(2-chlorophenyl)-6,7-dihydrothieno[3,2-c]pyridine-5(4H)-acetate sulfate (1:1).

One of Clopidogrel bisulfate structural formula is as follows:

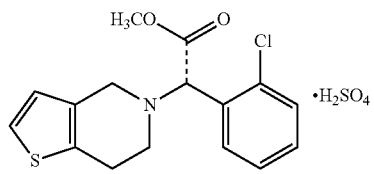

Clopidogrel bisulfate is an inhibitor of ADP-induced platelet aggregation acting by direct inhibition of adenosine diphosphate (ADP) binding to its receptor and of the subsequent ADP-mediated activation of the glycoprotein GPIIb/IIIa complex. In addition to ADP, Clopidogrel also block the release of ADP from the platelet activation caused by the proliferation, inhibit platelet aggregation induced by other agonists. Clopidogrel did not inhibit phosphodiesterase activity. Clopidogrel irreversibly modified by platelet ADP receptor.

Plavix (Clopidogrel Bisulphate tablet), a product of Sanofi-Aventis Company Limited, has been shown to reduce the rate of a combined endpoint of new ischemic stroke (fatal or not), new MI (fatal or not), and other vascular accidents resulting in death, and decrease the rate of a combined endpoint of cardiovascular death, MI, or stroke as well as the rate of a combined endpoint of cardiovascular death, MI, stroke, or refractory ischemia. Plavix also has been shown to reduce the rate of death from any cause and the rate of a combined endpoint of death, re-infarction or stroke.

In the Chinese market, Clopidogrel Bisulphate tablet of Shenzhen Salubris Pharmaceutical Company Limited-Talcom (the equivalent of 25 mg Clopidogrel) is used for preventing and treating heart, brain and other artery circulatory disturbance disease caused by platelet aggregate status.

U.S. Pat. No. 5,576,328 describes a method of preventing the occurrence of a secondary ischemic event by administration of Clopidogrel and one kind of medicinal acid salt and is incorporated herein as a reference.

U.S. Pat. No. 4,847,265 especially describes dextro-rotatory enantiomer of Clopidogrel and its pharmaceutically acceptable salt with platelet aggregation inhibiting activity and a process for preparation of this compound starting from the racemate and the pharmaceutical compositions containing it.

U.S. Pat. No. 6,429,210 and No. 6,504,030 claimed Clopiodgrel Bisulphate polymorphic form II and its preparation method.

U.S. Pat. No. 6,767,913 claimed the preparation method and pharmaceutics of Clopidogrel Bisulphate containing X Ray powder diffraction pattern with characteristic peaks and polymorphic form III, IV, V, VI, as well as preparation method of form II.

WO 2006/044548 provided solid premix based on containing Clopidogrel, there are at least one pharmaceutical excipient which is adsorbed on it.

WO 2004/098593 provided amorphous Clopidogrel sulphate, either or both of calcium stearate and magnesium stearate and one non-hygroscopic additive and at least one excipient.

WO 2007/008045 provided pharmaceutical containing Clopidogrel Bisulfate and pregelatinized starch.

WO 2008/059298 provided a formula for solid preparations containing Clopidogrel Bisulphate crystal form I as active ingredient, microcrystalline cellulose and aerosil as filler and adhesive, a disintegrant and a lubricant as other excipients.

The existing clopidogrel bisulphate tablet contains Clopidogrel Bisulphate, diluent, adhesive, glidant, disintegrant, and lubricant.

Plavix, manufactured by Sanofi-Aventis pharmaceutical Company Limited contains Mannitol, Microcrystalline cellulose, Hydroxy propyl cellulose, Polyethylene glycol 6000 and Hydrogenated castor oil in addition to Clopidogrel Bisulphate (From Plavix Label)

Clopidogrel being a thieno [3, 2-c] derivative exhibits rapid degradation when co-processed with certain excipients, such as alkaline metal containing salts for example magnesium stearate etc. Some patents do not use magnesium stearate to prevent Clopidogrel bisulfate from degrading.

Clopidogrel Bisulfate tablets of Shenzhen Salubris Pharmaceutical Company Limite-Taijia contains glycerol palmitic acid stearate and Colloidal Silicon Dioxide, preparing through grinding equal increments in order to increase the stability and safety of solid dosage form (from CN100400035).

U.S. Pat. No. 6,914,141 claimed one medicinal tablet which contain Clopidogrel Bisulphate and lubricant selected from zinc stearate, stearic acid and sodium stearoyl fumaric acid.

U.S. Pat. No. 4,591,592 claim ascorbic acid, benzoic acid, tartaric acid, fumaric acid, and citric acid can prevent degradation of the drug.

WO 0001364 claimed polyethylene glycol instead of magnesium stearate as lubricant. WO 2007/091279 claimed glyceryl dibehenate as lubricant. United States publication US20090264460 claimed one or some of stearic acid, magnesium stearate, zinc stearate, calcium stearate, sodium stearoyl fumaric acid, glycery behenate or hydrogenated vegetable oil as lubricant. Clopidogrel bisulfate contains a carbolic acidester easily hydrolyses in the presence of Clopidogrel acid (impurity A).

WO 2005/048992 claimed the formula of Clopidogrel Mesylate, Hydrobromide and Hydrochloride, and suggests coating Clopidogrel particles, granules or agglomerates with polyvinyl acetate or Polyvinyl alcohol and one hydrophobic ingredient such as hydrogenated vegetable oil.

WO 2008/072939 and WO 2008/072836 claimed that Clopidogrel having superior storage stability comprising Clopidogrel represented by the formula (1) below and β-cyclodextrin at an equivalence ratio from 1:1.0 to 1:2.5.

The biggest difficulty for Clopidogrel tablet manufacturing is that tablets containing Clopidogrel bisulfate will bond strongly to the punches and the dies of tablet compression machine, thus causing sticking and other kind of surface irregularities, resulting in final product quality issues. The root cause is attributed to Clopidogrel bisulfate which easily adheres to metal surfaces of compression equipment. Because of the compression forces exerted by the upper and lower punches during tablet compression, Clopidogrel bisulfate rapidly forms a film on the surface of the punches and/or die. And because of natural adhesion, the sticking increases over time and so causes quality issues on tablet surface. During commercial manufacture, sticking is a serious problem. It is better to solve the sticking problem during formulation and process development.

European publication for EP1970054 states that the choice of diluent is very important, as the combination use of some diluents such as mannitol, mannitol with lactose or microcrystalline cellulose will enhance the intrinsic stickiness tendency of Clopidogrel bisulfate. Considered that the lubricant can help to reduce frictional forces during compression and prevent the tablet to adhere the surface of punch and die, too. Therefore one of Clopidogrel bisulfate such as hydrobromide and hydrochloride can be used as raw material with lactose, stearic acid, and one or more of other excipients to prepare tablet. It also suggests using the dry granulation equipment to prepare stable Clopidogrel tablets to solve the problem of clopidogrel hydrobromide and clopidogrel hydrochloride tablets adhering to the punch and die of the tablet compression machine.

SUMMARY OF THE INVENTION

This invention relates to solving the problem of Clopidogrel bisulfate sticking on the punch and/or the die of tablet compression machine during tablet manufacturing process.

It is known to one skilled in the art that the most difficult problem in preparation technology of Clopidogrel bisulfate tablets is in that the Clopidogrel bisulfate tends to adhere strongly to the punch and/or the die surfaces of a conventional tablet compression machine, causing picking, sticking or other kinds of surface irregularities on tablets, which consequently leads to poor final product quality. The root cause is attributed to the extremely hygroscopic nature of Clopidogrel bisulfates which makes the material extremely adhesive to the metal surfaces of the punch and/or the die, and further compression between the upper/lower punch and the die causes the Clopidogrel bisulfate to rapidly form a film on the surface of the punch and die therefore cause a sticking problem.

There are several ways to reduce the Clopidogrel bisulfate adhesion to the punch and/or the die. One is increasing the binder amount in the formulation to form large, strong granules of Clopidogrel bisulfate therefore reduce the exposed surface area of Clopidogrel containing particles. Another way is to cover the Clopidogrel particle surface with one or more water insoluble excipients.

This invention has provided a new method of preparing Clopidogrel bisulfate tablet (oral and other). It uses an antiadherent and coating agent, known as Colloidal Silicon Dioxide, to isolate Clopidogrel bisulfate raw material from the surrounding environment, therefore overcoming the above mentioned sticking problem during tablet manufacture.

Colloidal Silicon Dioxide has good flowability. Its superiority resides in its uniform small particle size distribution with a very large specific surface area, which enables it to be uniformly distributed onto the surface of Clopidogrel bisulfate particles of only several dozen microns in size. The Colloidal Silicon Dioxide coverage of Clopidogrel bisulfate particles reduces Clopidogrel bisulfate particle surface area exposure, therefore lowering the probability of Clopidogrel bisulfate sticking to metal surfaces. The angle of repose of Clopidgrel salt was greater than 45 as is, and declined to 40 after being mixed with Colloidal Silicon Dioxide, thus increasing the flowability. As a result, the addition of Colloidal Silicon Dioxide decreased Clopidogrel bisulfate adhesion to the punch and die.

In some embodiment, the average particle size of Clopidogrel bisulfate is 10-100 µm, preferably 20-80 µm.

This present invention in preparation of Clopidogrel bisulfate tablet contains following components: Clopidogrel bisulfate, anti-adherents/coating agent, diluents, adhesives, glidants, disintegrants, lubricants.

The Clopidogrel bisulfate as described contains equivalent of Clopidogrel 75-300 mg.

The anti-adherent/coating agent/glidant is Colloidal Silicon Dioxide. The particle size of Colloidal Silicon Dioxide is about 7-16 nm and with specific surface area of 200-400 $m^2/g$. The average particle size of the Clopidogrel bisulfate is about 76 µm. Based on the particle size of Colloidal Silicon Dioxide and Clopidogrel bisulfate, the ratio of Colloidal Silicon Dioxide surface area of 250 mg vs. the surface area of Clopidogrel bisulfate particle is about 84-148 times (calculated by mg/tablet). The Colloidal Silicon Dioxide amount is 0.3%-8% by weight of the of Clopidogrel bisulfate, preferably 0.5% -5% by weight.

The weight of both Colloidal Silicon Dioxide and Clopidogrel bisulfate are 90%-100% w/w of that of the premix granule of Clopidogrel bisulfate, preferably 95-100%, and even more preferably 99-100%.

The diluents are Lactose, pregelatinized Starch, Microcrystalline cellulose, preferably Lactose and Microcrystalline cellulose. Based on the tablet total weight, 5%-39% by weight, preferably 10%-30% by weight of Microcrystalline cellulose.

The binder described can be any pharmaceutically acceptable binder such as PVP K30, Hydroxypropyl cellulose (HPC), or one or more low viscosity HPMC, preferably HPC. Based on the tablet total weight, the binder should be 0.5% -2% by weight, preferably 0.6%-1.5% % by weight of the tablet.

The disintegrants described can be any pharmaceutically acceptable disintegrant, such as low density Hydroxypropyl cellulose, Sodium starch Glycolate, Crospovidone, Croscarmellose sodium, preferably Crospovidone and/or Croscarmellose sodium. Based on the tablet total weight, the disintegrant should be 0.8%-5.0% by weight, preferably 1.0% -4.0% by weight of the tablet.

The lubricants described can be any pharmaceutically acceptable lubricant, preferably hydrogenated vegetable oil, and Sodium lauryl sulphate. Based on the Clopidogrel bisulfate tablet total weight, the lubricant should be 0 5%-6.8% by weight of the tablet.

One aspect of this invention describes the formulation of Clopidogrel bisulfate tablet as follows:
   25-50 weight % Clopidogrel bisulfate;
   1-4 weight % Colloidal Silicon Dioxide as an anti-adherent/covering agent;
   20-30 weight % Lactose and 10-30 weight % Microcrystalline cellulose;
   0.6-1.5 weight % Hydroxypropyl Cellulose;
   0.2-0.5 weight % Colloidal Silicon Dioxide as a glidant; and
   1.2-4.0 weight % Crospovidone.

One aspect of this invention describes the manufacture of Clopidogrel bisulfate tablet as follows:
   1. Separately mix the Clopidogrel bisulfate and Colloidal Silicon Dioxide until the Colloidal Silicon Dioxide is uniformly distributed on the surface of the Clopidogrel particles.

2. Add the diluent and mix with the prepared binder solution to granulate the mixture.
3. The wet granules are dried, milled, and blended with disintegrant, lubricant and glidant. After uniformly blending the granules, this blend is compressed to form tablets.

Preferably the manufacturing environment relative humidity should below 45% RH. The Clopidogrel bisulfate tablet of this invention needs to be coated by a colored film so that the tablet can be easily identified and to protect from direct contact with air and moisture. The film coating does not affect the release of drug from tablet as it quickly dissolves in stomach.

The raw materials and excipients used in this invention are commercially available.

This positive progressive effect of this invention lies in:

This invention describes Clopidogrel bisulfate tablets that avoid tablet surface defects causing by sticking because the drug is mixed directly with Colloidal Silicon Dioxide as antiadherent/coating agent. The surfaces of tablet are smooth and debossing clearly.

DETAILED DESCRIPTION OF THE INVENTION

The invention is further illustrated by the following examples but not be restricted by them.

The Colloidal Silicon Dioxide used in the examples are manufactured by Evonik Degussa Co., Ltd. Its trade name is Aerosil 200® Pharma.

The method used in this invention to indicate s sticking is:

| Tablets yield the following results for examination of 100 tablets. | Result |
| --- | --- |
| Continuous tablet compression for 10 minutes, tablets with indistinct debossing obvious >80T | sticking |
| Continuous tablet compression for 10 minutes, tablet with indistinct debossing obvious between 50~80T | slight improvement |
| Continuous tablet compression for 10 minutes, tablet with indistinct debossing obvious between 20~50T | improvement |
| Continuous tablet compression for 10 minutes, tablet with indistinct debossing obvious between ≤20T | almost no-sticking |
| Continuous tablet compression for 30 minutes, no tablets with indistinct debossing obvious | no sticking |

The following table contains results of sticking when Clopidogrel bisulfate raw material is premixed with different ratios Colloidal Silicon Dioxide based on tablet weight, for Clopidogrel bisulfate tablets prepared according to the formula and technology from international publication WO2008059298:

From the table, according to the method of determining sticking on the punch and/or die, when there is no Colloidal Silicon Dioxide, the tablet was sticking on punch and/or die; when Colloidal Silicon Dioxide is only as glidant in the tablet, the tablet shows slight sticking on punch and/or die; when Colloidal Silicon Dioxide is premixed with raw material as anti-adherent/coating agent, even if the content is only half of the content of glidant in each tablet, the sticking decreased; the sticking also decreased as the same amount of glidant was used at the same time. When the content of glidant was not changed, the sticking has been solved completely by increasing the content of Colloidal Silicon Dioxide as anti-adherent/coating agent. It is known that Colloidal Silicon Dioxide as anti-adherent/coating agent was premixed with raw material to make it uniformly dispersed on the surface of drug material particles. Even if the quantity of Colloidal Silicon Dioxide is only 0.75 mg/tablet, the sticking also decreased on the punch and/or die. The example applied the formulation of international publication WO2008059298, the sticking has not been improved during the process of compression.

It is shown in the above table that premixing Colloidal Silicon Dioxide with Microcrystalline cellulose as diluent and adhesive according to international publication WO2008059298 method of preparing tablets, the sticking has not been improved during the process of compression. The tablets prepared according to the present invention formulation and technology are better than the above tablets in solving sticking on punch and/or die. So the tablet quality is better. The reason is that, the function of Colloidal Silicon Dioxide is completely different with different manufacturing technology and it is also different affect on the tablet quality although using the same Colloidal Silicon Dioxide.

Operation steps:

EXAMPLE 1

Preparing Clopidogrel Bisulfate Tablets 97.88 g Clopidogrel bisulfate was mixed with 60.0 g Lactose, 40.00 g Microsrystalline Cellulose. Adding the 10% prepared Hydroxypropyl Cellulose solution and granulation. The granules were dried and screening. Blending with 26.00 g Microcrystalline Cellulose, 6.00 g Crospovidone, 17.00 g of Hydrogenated Vegetable Oil and Sodium Lauryl Sulphate and compression. The tablet weight is 250 mg with diameter 9 mm.

EXAMPLE 2

97.88 g Clopidogrel bisulfate was mixed with 60.00 g Lactose, 40 g of Microcrystalline Cellulose. Adding the 10%

TABLE 1

Clopidogrel bisulfate tablet containing different ratio of Colloidal Silicon Dioxide

| Funcation | Examples | | | | | | |
| --- | --- | --- | --- | --- | --- | --- | --- |
| | 1 | 2 | 3 | 4 mg/table | 5 | 6 | 7 |
| Antiadherent/covering agent | — | — | 0.75 | 0.75 | 2.50 | 5.00 | — |
| Glidant | — | 1.50 | — | 0.75 | 0.75 | 0.75 | — |
| According to WO2008059298 | — | — | — | — | — | — | 4.98 |
| Result | sticking | Slight sticking | Decrease | Decrease | No sticking | No sticking | sticking | prepared Hydroxypropyl Cellulose solution and granulation. The granules were dried and blended with Aerosil (1.5 g, the weight equivalent to 0.6% of tablet weight), Microcrystalline Cellulose 26.00 g, Crospovidone 6.00 g, 17.00 g Hydrogenated Vegetable Oil and Sodium Lauryl Sulphate. Then compression with tablet weight 250 mg and diameter 9 mm.

EXAMPLE 3

97.88 g Clopidogrel bisulfate was premixed with Aerosil, (0.75 g, equivalent to 0.3% of tablet weight), then mixed with Lactose 60.00 g, Microcrystalline Cellulose 40.00 g. Adding the 10% prepared Hydroxypropyl Cellulose solution to and granulation. The granules were dried and blended with Microcrystalline Cellulose 26.00 g, Crospovidone 6.00 g, 17.00 g Hydrogenated Vegetable Oil and Sodium Lauryl Sulphate. Then compression with tablet weight 250 mg with diameter 9 mm.

EXAMPLE 4

97.88 g Clopidogrel bisulfate was premixed with Aerosil (0.75 g, equivalent to 0.3% of tablet weight), then mixed with Lactose 60.00 g, Microcrystalline Cellulose 40.00 g. Adding the 10% prepared Hydroxypropyl Cellulose solution and granulation. The granules were dried and blended with Aerosil (0.75 g, equivalent to 0.3% of tablet weight), Microcrystalline Cellulose 26.00 g, Crospovidone 6.00 g, 17.00 g Hydrogenated Vegetable Oil and Sodium Lauryl Sulphate. Then compression with tablet weight 250 mg with diameter 9 mm.

EXAMPLE 5

97.88 g Clopidogrel bisulfate was premixed with Aerosil (2.50 g, equivalent to 1.0% of tablet weight), then mixed with Lactose 60.00 g, Microcrystalline Cellulose 40.00 g. Adding the 10% prepared Hydroxypropyl Cellulose solution and granulation. The granules were dried and blended with Aerosil (0.75 g, equivalent to 0.3% of tablet weight), Microcrystalline Cellulose 26.00 g, Crospovidone 6.00 g, 17.00 g of Hydrogenated Vegetable Oil and Sodium Lauryl Sulphate. Then compression with tablet weight 250 mg with diameter 9 mm and coated.

EXAMPLE 6

97.88 g Clopidogrel bisulfate was premixed with Aerosil (5.00 g, equivalent to 2.0% of tablet weight), then mixed with Lactose 60.00 g, Microcrystalline Cellulose 40.00 g. Adding the 10% prepared Hydroxypropyl Cellulose solution and granulation. The granules were dried and blended with Aerosil (0.75 g, equivalent to 0.3% of tablet weight), Microcrystalline Cellulose 26.00 g, Crospovidone 6.00 g, 17.00 g of Hydrogenated Vegetable Oil and Sodium Lauryl Sulphate. Then compression with tablet weight 250 mg with diameter 9 mm.

EXAMPLE 7

According to the formula and technology of International publication WO2008059298, premixing the Aerosil (5.00 g, equivalent to 1.56% of tablet weight) with Microcrystalline Cellulose 50 g and passed through 0.5 mm sieve. This mixture is further blended with Clopidogrel bisulfate 97.9 g, 144.2 g Microcrystalline Cellulose, 12 g L-HPC, 12 g Hydrogenated Vegetable Oil. Blending speed is 20 rpm and blending time is 20 minutes. Then compression with tablet weight 320 mg with diameter 10 mm.

Effects of Implementation of the Examples

According to the preparation described in example 1, Clopidogrel bisulfate tablet without Aerosil shows sticking on the punch soon after starting compression.

According to the preparation described in example 2, Clopidogrel bisulfate tablet with Aerosil (weight equivalent to 0.6% of tablet weight) still shows sticking on punch after 10 minutes of compression.

According to the preparation described in example 3, Clopidogrel bisulfate premixing with Aerosil (weight equivalent to 0.3% of tablet weight), the tablet sticking decreases during compression.

According to the preparation described in example 4, Clopidogrel bisulfate premixing with Aerosil (weight equivalent to 0.3% of tablet weight) and the same quantity of Aerosil in the external phase, the sticking decreased during compressing similar to example 3.

According to the preparation described in example 5 and example 6, Clopidogrel bisulfate premixed with Aerosil (weight equivalent to 1.0% -2.0% of tablet weight) and external phase Aerosil (weight equivalent to 0.3% of tablet weight), the tablets showed no sticking on punch.

According to the preparation described in example 7, Aerosil premixed with microcrystalline cellulose at the ratio of 1:10 and sieved, the quantity of Aerosil is equivalent to 1.56% of tablet weight, then mixed with Clopidogrel bisulfate raw materials and other excipients. The tablet is sticking on punch during compression.

What is claimed is:

1. A method for preparing a pharmaceutical composition of Clopidogrel bisulfate, comprising the steps of:
   (a) mixing Colloidal Silicon Dioxide and Clopidogrel bisulfate to form a premix granule;
   wherein the premix granule contains the following components: Clopidogrel bisulfate having an average particle size of 10-100 μm, and Colloidal Silicon Dioxide for covering Clopidogrel bisulfate,
   wherein the weight of Colloidal Silicon Dioxide is 0.5%-10% w/w of that of Clopidogrel bisulfate;
   wherein the average particle size of Clopidogrel bisulfate is 10-100 μm; and wherein the particle size of Colloidal Silicon Dioxide is 7-16 nm and with a surface area of 200-400 m$^2$/g;
   (b) mixing the premix granule obtained from step (a) with diluents, followed by adding an alcohol solution of a binder for wet granulation to obtain a wet granule;
   (c) drying the wet granule obtained from step (b) followed by screening to obtain a dry granule;
   (d) mixing the dry granule obtained from step (c) with 0.2-0.5 weight % Colloidal Silicon Dioxide as a glidant, disintegrant and lubricants, followed by compressing to obtain a Clopidogrel bisulfate tablet; and
   (e) Optionally coating the tablet obtained from step (d) to obtain a film-coated final tablet.

2. The method of claim 1, wherein the weight of Colloidal Silicon Dioxide is 1.0%-5% w/w of that of Clopidogrel bisulfate.

3. The method of claim 1, wherein the weight of both Colloidal Silicon Dioxide and Clopidogrel bisulfate is 90%-100% w/w of that of the premix granule.

4. The method of claim 1, wherein the composition is a solid formulation.

5. The method of claim 4, wherein the composition is an oral tablet dosage form.

6. The method of claim 5, wherein the composition contains the following ingredients:
   25-50 weight % Clopidogrel bisulfate,
   1-4 weight % Colloidal Silicon Dioxide as an anti-adherent/covering agent,
   20-30 weight % Lactose and 10-30 weight % microcrystalline cellulose,
   0.6-1.5 weight % Hydroxypropyl Cellulose,
   1.2-4.0 weight % Crospovidone.

7. A method for preparing a pharmaceutical composition of Clopidogrel bisulfate, comprising the steps of:
   (a) separately mixing Clopidogrel bisulfate and Colloidal Silicon Dioxide until the Colloidal Silicon Dioxide is uniformly distributed on and covers the surface of the Clopidogrel bisulfate particles to form a premix granule,
   wherein the premix granule consists of the Colloidal Silicon Dioxide as a surface covering agent and the Clopidogrel bisulfate having an average particle size of 10-100 μm, and
   wherein the Clopidogrel bisulfate in the premix granule is 25-50 weight %; wherein the Colloidal Silicon Dioxide is 1-4 weight %; wherein the particle size of Colloidal Silicon Dioxide is 7-16 nm and with a surface area of 200-400 m$^2$/g;
   (b) mixing the premix granule obtained from step (a) with 20-30 weight % of Lactose and 10-30 weight % of microcrystalline cellulose, followed by adding an alcohol solution of 0.6-1.5 weight % of Hydroxypropyl Cellulose to obtain a wet granule;
   (c) drying the wet granule obtained from step (b) followed by screening to obtain a dry granule;
   (d) mixing the dry granule obtained from step (c) with 0.2-0.5 weight % Colloidal Silicon Dioxide as a glidant, 1.2-4.0 weight % of Crospovidone, and microcrystalline cellulose, followed by compressing to obtain a Clopidogrel bisulfate tablet; and
   wherein the total of microcrystalline cellulose used in steps (b) and (d) is 10-30 weight %,
   wherein the weight% is based on tablet weight.

8. The method of claim 7, wherein
   in step (a), the Colloidal Silicon Dioxide in the premix granule as a covering agent is 1.0-2.0 weight %, and
   in step (d), the Colloidal Silicon Dioxide used as a glidant is 0.5 weight %.

9. A pharmaceutical composition of Clopidogrel bisulfate prepared according to the method of claim 1.

10. The pharmaceutical composition of claim 9, wherein the composition is a solid formulation.

11. The pharmaceutical composition of claim 9, wherein the composition is an oral tablet dosage form.

12. A pharmaceutical composition of Clopidogrel bisulfate prepared according to the method of claim 7.

* * * * *